(12) United States Patent
Jeong et al.

(10) Patent No.: US 11,666,275 B2
(45) Date of Patent: Jun. 6, 2023

(54) ELECTRONIC DEVICE HAVING ELECTRODE MEASURING BIOLOGICAL SIGNAL

(71) Applicant: Samsung Electronics Co., Ltd., Suwon-si (KR)

(72) Inventors: Injo Jeong, Suwon-si (KR); Seongwook Jo, Suwon-si (KR); Hyunguk Yoo, Suwon-si (KR); Younghyun Kim, Suwon-si (KR); Suho Lee, Suwon-si (KR); Jeahyuck Lee, Suwon-si (KR); Jeehoon Lee, Suwon-si (KR); Hyunjun Jung, Suwon-si (KR); Shinhee Cho, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 239 days.

(21) Appl. No.: 16/889,309

(22) Filed: Jun. 1, 2020

(65) Prior Publication Data

US 2021/0030359 A1 Feb. 4, 2021

(30) Foreign Application Priority Data

Jul. 31, 2019 (KR) .......................... 10-2019-0093204

(51) Int. Cl.
*A61B 5/00* (2006.01)
*A61B 5/024* (2006.01)
*A61B 5/259* (2021.01)

(52) U.S. Cl.
CPC .......... *A61B 5/681* (2013.01); *A61B 5/02416* (2013.01); *A61B 5/259* (2021.01);
(Continued)

(58) Field of Classification Search
CPC ..... A61B 5/681; A61B 5/02416; A61B 5/259; A61B 5/742; A61B 2560/04;
(Continued)

(56) References Cited

U.S. PATENT DOCUMENTS

| 8,773,847 B2 | 7/2014 | Byun et al. |
| 9,420,956 B2 | 8/2016 | Gopalakrishnan et al. |

(Continued)

FOREIGN PATENT DOCUMENTS

| CN | 104917301 A | 9/2015 |
| EP | 2 367 292 A2 | 9/2011 |

(Continued)

OTHER PUBLICATIONS

International Search Report dated Sep. 15, 2020, issued in International Application No. PCT/KR2020/006802.

(Continued)

*Primary Examiner* — Eric F Winakur
*Assistant Examiner* — Abid A Mustansir
(74) *Attorney, Agent, or Firm* — Jefferson IP Law, LLP

(57) ABSTRACT

An electronic device is provided. The electronic device includes a housing including a first surface facing a first direction, a second surface facing a second direction opposite to the first surface, and a third surface connecting the first surface and the second surface to form a space in the housing, a display viewable in the first direction through the first surface of the housing, a printed circuit board (PCB) disposed in the space, a glass covering at least a part of the second surface of the housing and including a fourth surface facing the first direction and a fifth surface facing the second direction, a high-hardness member disposed on the fifth surface, a first conductive member disposed between the
(Continued)

high-hardness member and the glass, and a second conductive member disposed on the fourth surface and electrically connected to the PCB.

25 Claims, 18 Drawing Sheets

(52) U.S. Cl.
CPC .......... *A61B 5/742* (2013.01); *A61B 2560/04* (2013.01); *A61B 2562/166* (2013.01)

(58) Field of Classification Search
CPC . A61B 2562/166; A61B 5/002; A61B 5/0022; A61B 5/256; A61B 5/28; A61B 5/021; A61B 5/02438; A61B 5/14542; A61B 5/14551; A61B 5/332; A61B 5/7455; A61B 5/0059; A61B 5/25; A61B 5/263; A61B 5/265; A61B 2562/0209; A61B 5/7445

See application file for complete search history.

(56) References Cited

U.S. PATENT DOCUMENTS

| | | |
|---|---|---|
| 10,020,572 B2 | 7/2018 | Kim et al. |
| 10,159,415 B2 | 12/2018 | Gopalakrishnan et al. |
| 10,333,211 B2 | 6/2019 | Kim et al. |
| 10,426,359 B2 | 10/2019 | Gopalakrishnan et al. |
| 10,727,576 B2 | 7/2020 | Kim et al. |
| 2016/0066852 A1 | 3/2016 | Cheng et al. |
| 2019/0041917 A1 | 2/2019 | Chung |
| 2019/0072912 A1 | 3/2019 | Pandya et al. |
| 2019/0074729 A1 | 3/2019 | Wittenberg et al. |
| 2019/0090806 A1* | 3/2019 | Clavelle ............... G04G 9/0088 |
| 2019/0094969 A1 | 3/2019 | Wen et al. |
| 2019/0101870 A1 | 4/2019 | Pandya et al. |
| 2019/0129470 A1* | 5/2019 | Hasei ..................... G04R 20/02 |
| 2019/0393730 A1 | 12/2019 | Wittenberg et al. |
| 2020/0159331 A1 | 5/2020 | Wen et al. |

FOREIGN PATENT DOCUMENTS

| | | |
|---|---|---|
| EP | 3 454 454 A1 | 3/2019 |
| JP | S5990155 U | 6/1984 |
| JP | 2018102404 A | 7/2018 |
| KR | 10-2016-0069623 A | 6/2016 |

OTHER PUBLICATIONS

Extended European Search Report dated Sep. 19, 2022, issued in European Application No. 20847709.1.

* cited by examiner

ELECTRONIC DEVICE HAVING ELECTRODE MEASURING BIOLOGICAL SIGNAL

CROSS-REFERENCE TO RELATED APPLICATION(S)

This application is based on and claims priority under 35 U.S.C. § 119(a) of a Korean patent application number 10-2019-0093204, filed on Jul. 31, 2019, in the Korean Intellectual Property Office, the disclosure of which is incorporated by reference herein its entirety.

BACKGROUND

1. Field

The disclosure relates to an electronic device having an electrode measuring a biological signal.

2. Description of Related Art

A wearable electronic device that are carried or used in a state worn by a user among electronic devices are increasing. The wearable electronic device includes various types of electronic devices such as a smart watch, a smart band, a smart glass, and a chest patch. The wearable electronic device may have an electrode for measuring biometric information of the user. For example, the smart watch may place the electrode for measuring a user's electrocardiogram (ECG) in a portion in contact with a user's wrist.

A current related to the user's biometric information may be generated. For example, the current may be generated by a user's heartbeat. The generated current may form a voltage by impedance between the user and the wearable electronic device. When the current generated by the user's biometric information is sensed by the electrode of the wearable electronic device, the wearable electronic device may process the sensed current in an amplifying circuit connected to the electrode to obtain a voltage value obtained thereby. The wearable electronic device may process the user's biometric information using a maximum value of the obtained voltage, a minimum value of the obtained voltage, an amount of change in the obtained voltage, and/or a reference voltage. For example, the smart watch may detect a resistance of the electrode, a resistance of a contact part between the smart watch and the user's wrist, a current formed by an electric field (E-field) formed in the contact part between the smart watch and the user's wrist. The smart watch may acquire a voltage waveform that amplifies the current sensed by the electrode in the amplifying circuit. The smart watch may measure the user's electrocardiogram using a maximum value of the acquired voltage waveform, a minimum value of the acquired voltage waveform, and a change amount over time of the acquired voltage waveform.

The above information is presented as background information only to assist with an understanding of the disclosure. No determination has been made, and no assertion is made, as to whether any of the above might be applicable as prior art with regard to the disclosure.

SUMMARY

An electrode of a wearable electronic device may maintain a state in contact with a user's body for a long time to measure a user's biometric information. Damage to the electrode may occur, such as wear of an electrode surface due to friction and corrosion of the electrode due to foreign matter such as sweat while in contact with the user's body. Accordingly, the surface of the electrode of the wearable electronic device may be designed to have a hardness greater than or equal to a specified hardness.

In addition, the electrode of the wearable electronic device may be measured by a voltage based on the user's biometric information. As a resistance of the electrode decreases, the voltage based on the user's biometric information may be measured more accurately. Accordingly, the electrode of the wearable electronic device may be designed to have a resistance less than or equal to a specified resistance.

Aspects of the disclosure are to address at least the above-mentioned problems and/or disadvantages and to provide at least the advantages described below. Accordingly, an aspect of the disclosure is to provide an electronic device having an electrode whose surface has a specified hardness or more and an electrode having a resistance of a specified resistance or less.

In accordance with an aspect of the disclosure, an electronic device may include a housing that includes a first surface facing a first direction, a second surface facing a second direction opposite to the first surface, and a third surface connecting the first surface and the second surface to form a space in the housing, a display viewed in the first direction through the first surface of the housing, a printed circuit board (PCB) disposed in the space, a glass that covers at least a part of the second surface of the housing and includes a fourth surface facing the first direction and a fifth surface facing the second direction, a high-hardness member disposed on the fifth surface, a first conductive member disposed between the high-hardness member and the glass, and a second conductive member disposed on the fourth surface and electrically connected to the PCB.

In accordance with another aspect of the disclosure, a wearable electronic device may include a housing that includes a first surface facing a first direction, a second surface facing a second direction opposite to the first surface, and a third surface connecting the first surface and the second surface to form a space in the housing, a display viewed in the first direction through the first surface of the housing, a PCB disposed in the space, a glass that covers at least a part of the second surface of the housing and includes a fourth surface facing the first direction and a fifth surface facing the second direction, a first electrode disposed on the glass and having a first voltage, a second electrode disposed on the glass to be adjacent to the first electrode and having a ground voltage, and a third electrode having a second voltage having a polarity opposite to a polarity of the first voltage based on the ground voltage, and the first electrode may include a high-hardness member disposed on the fifth surface, a first conductive member disposed between the high-hardness member and the glass, and a second conductive member disposed on the fourth surface to be electrically connected to the PCB.

In accordance with another aspect of the disclosure, an electronic device may include a housing that includes a first surface facing a first direction, a second surface facing a second direction opposite to the first surface, and a third surface connecting the first surface and the second surface to form a space in the housing, a display viewed in the first direction through the first surface of the housing, a PCB disposed in the space, a glass that covers at least a part of the second surface of the housing and includes a fourth surface facing the first direction and a fifth surface facing the second direction, a lower electrode disposed on the fifth surface, and an upper electrode disposed on the fourth surface to be in contact with the lower electrode at a boundary line, which is in contact with the housing, to be electrically connected to the PCB.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which.

Throughout the drawings, it should be noted that like reference numbers are used to depict the same or similar elements, features, and structures.

DETAILED DESCRIPTION

The following description with reference to accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Figure 1:
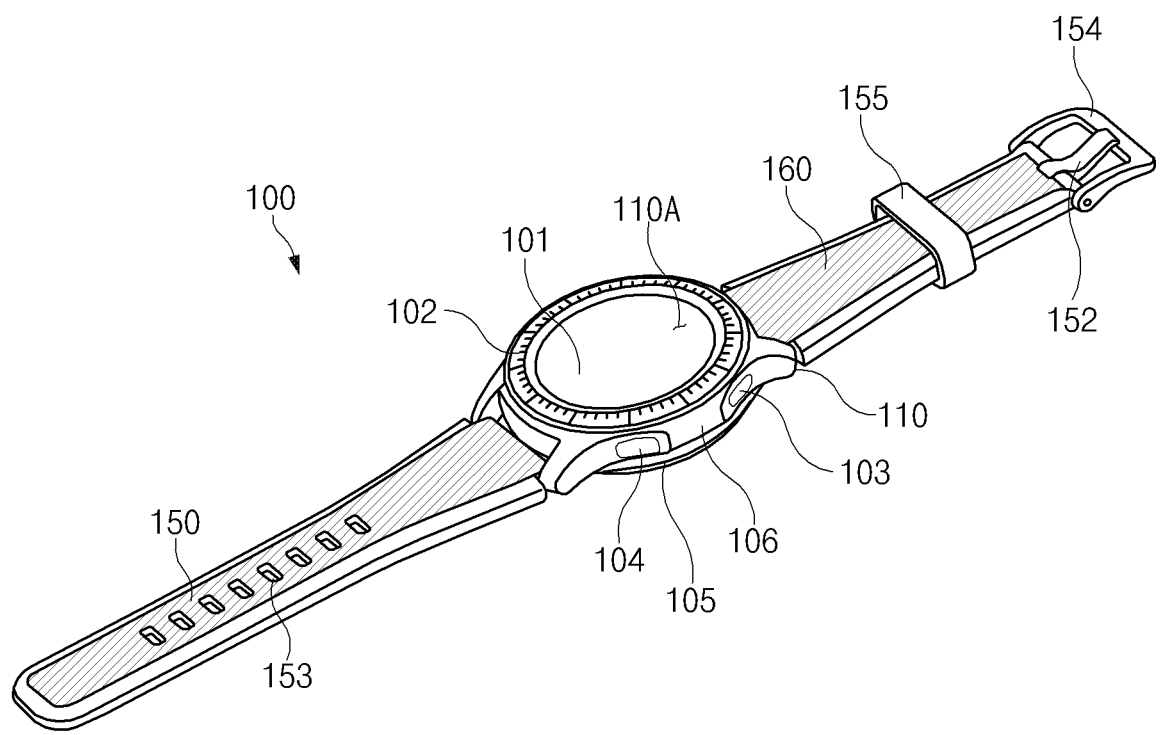
FIG. 1 is a perspective view of a front side of a mobile electronic device according to an embodiment of the disclosure.

FIG. 1 is a perspective view of a front side of a mobile electronic device according to an embodiment of the disclosure.

Figure 2:
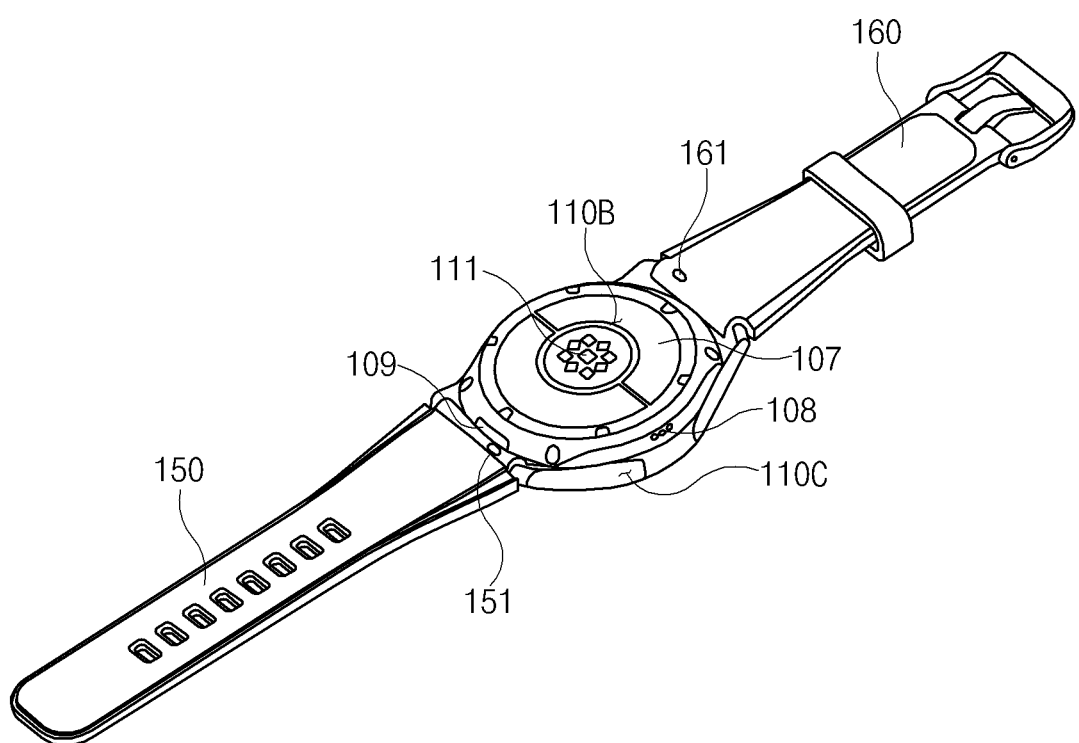
FIG. 2 is a perspective view of a rear side of the electronic device of FIG. 1 according to an embodiment of the disclosure.

FIG. 2 is a perspective view of a rear side of the electronic device of FIG. 1 according to an embodiment of the disclosure.

Referring to FIGS. 1 and 2, an electronic device 100 according to an embodiment may include a housing 110 including a first surface (or front surface) 110A, a second surface (or rear surface) 110B, and a side surface 110C surrounding a space between the first surface 110A and the second surface 110B, and coupling members 150 and 160, which is connected to at least a part of the housing 110 and configured to detachably connect the electronic device 100 to a user's body part (e.g., wrist, ankle, etc.). In another embodiment (not illustrated), the housing may refer to a structure forming some of the first surface 110A, the second surface 110B, and the side surfaces 110C of FIG. 1. According to an embodiment, the first surface 110A may be formed by a front plate 101 (e.g., a glass plate including various coating layers, or a polymer plate) at least partially substantially transparent. The second surface 110B may be formed by a substantially opaque back plate 107. The back plate 107 may be formed by, for example, coated or colored glass, ceramic, polymer, metal (e.g., aluminum, stainless steel (STS), or magnesium), or a combination of at least two of the above materials. The side surface 110C may be formed by a side bezel structure (or a "side member") 106 that is coupled to the front plate 101 and the back plate 107 and includes metal and/or polymer. In some embodiments, the back plate 107 and the side bezel structure 106 may be integrally formed and include the same material (e.g., a metal material such as aluminum). The coupling members 150 and 160 may be formed of various materials and shapes. The coupling members 150 and 160 may be formed of woven fabric, leather, rubber, urethane, metal, ceramic, or a combination of at least two of the above materials to form a unitary and a plurality of unit links, which are flexible with each other.

According to an embodiment, the electronic device 100 may include a display 120 (see FIG. 3), audio modules including a microphone hole 105 and a speaker hole 108, a sensor module 111, key input devices 102, 103, and 104, and at least one connector hole 109. In some embodiments, the electronic device 100 may omit at least one of the components (e.g., the key input devices 102, 103, and 104, the connector hole 109, or the sensor module 111) or may further include other components.

For example, the display 120 may be exposed through a significant portion of the front plate 101. A shape of the display 120 may be a shape corresponding to a shape of the front plate 101, and may have various shapes such as a circular shape, an oval shape, or a polygonal shape. The display 120 may be combined with or disposed adjacent to a touch sensing circuit, a pressure sensor capable of measuring an intensity (pressure) of a touch, and/or a fingerprint sensor.

The audio modules including the microphone hole 105 and the speaker hole 108 may include the microphone hole 105 and the speaker hole 108. In the microphone hole 105, a microphone for acquiring external sound may be disposed therein, and in some embodiments, a plurality of microphones may be arranged to sense a direction of sound. The speaker hole 108 may be used as an external speaker and a call receiver. In some embodiments, the speaker hole 108 and the microphone hole 105 may be implemented as one hole, or a speaker may be included without the speaker hole 108 (e.g., piezo speaker).

The sensor module 111 may generate an electrical signal or data value responding to an internal operating state of the electronic device 100 or an external environmental state. The sensor module 111 may include, for example, the biosensor module 111 (e.g., a heart rate (HR) monitor (HRM) sensor) disposed on the second surface 110B of the housing 110. The electronic device 100 may further include, a sensor module not illustrated, at least one of a gesture sensor, a gyro sensor, a barometric pressure sensor, a magnetic sensor, an acceleration sensor, a grip sensor, a color sensor, an infrared (IR) sensor, a bio sensor, a temperature sensor, a humidity sensor, or an illuminance sensor.

The key input devices 102, 103, and 104 may include the wheel key 102 disposed on the first surface 110A of the housing 110 and rotatable in at least one direction and/or the side key buttons 103 and 104 disposed on the side surface 110C of the housing 110. The wheel key may have a shape corresponding to the shape of the front plate 101. In another embodiment, the electronic device 100 may not include some or all of the key input devices 102, 103, and 104 mentioned above, and the key input devices 102, 103, and 104 that are not included may be implemented in other forms, such as a soft key, on the display 120. The connector hole 109 may accommodate a connector (e.g., a universal serial bus (USB) connector) for transmitting and receiving power and/or data to and from an external electronic device, and another connector hole (not shown) which is capable of accommodating a connector for transmitting and receiving audio signals to and from the external electronic device may be provided. The electronic device 100 may further include, for example, a connector cover (not shown) that covers at least a part of the connector hole 109 and blocks inflow of foreign substances into the connector hole.

The coupling members 150 and 160 may be detachably coupled to at least a part of the housing 110 using locking members 151 and 161. The coupling members 150 and 160 may include one or more of a fastening member 152, a fastening member coupling hole 153, a band guide member 154, and a band fastening loop 155.

The fastening member 152 may be configured to fasten the housing 110 and the coupling members 150 and 160 to the part of the user's body (e.g., wrist, ankle, etc.). The fastening member coupling hole 153 may fasten the housing 110 and the coupling members 150 and 160 to the part of the user's body corresponding to the fastening member 152. The band guide member 154 may be configured to limit a range of movement of the fastening member 152 when the fastening member 152 is combined with the fastening member coupling hole 153, to allow the coupling members 150 and 160 to be tightly fastened to the part of the user's body. The band fastening loop 155 may limit the range of movement of the coupling members 150 and 160 while the fastening member 152 and the fastening member coupling hole 153 are fastened.

Figure 3:
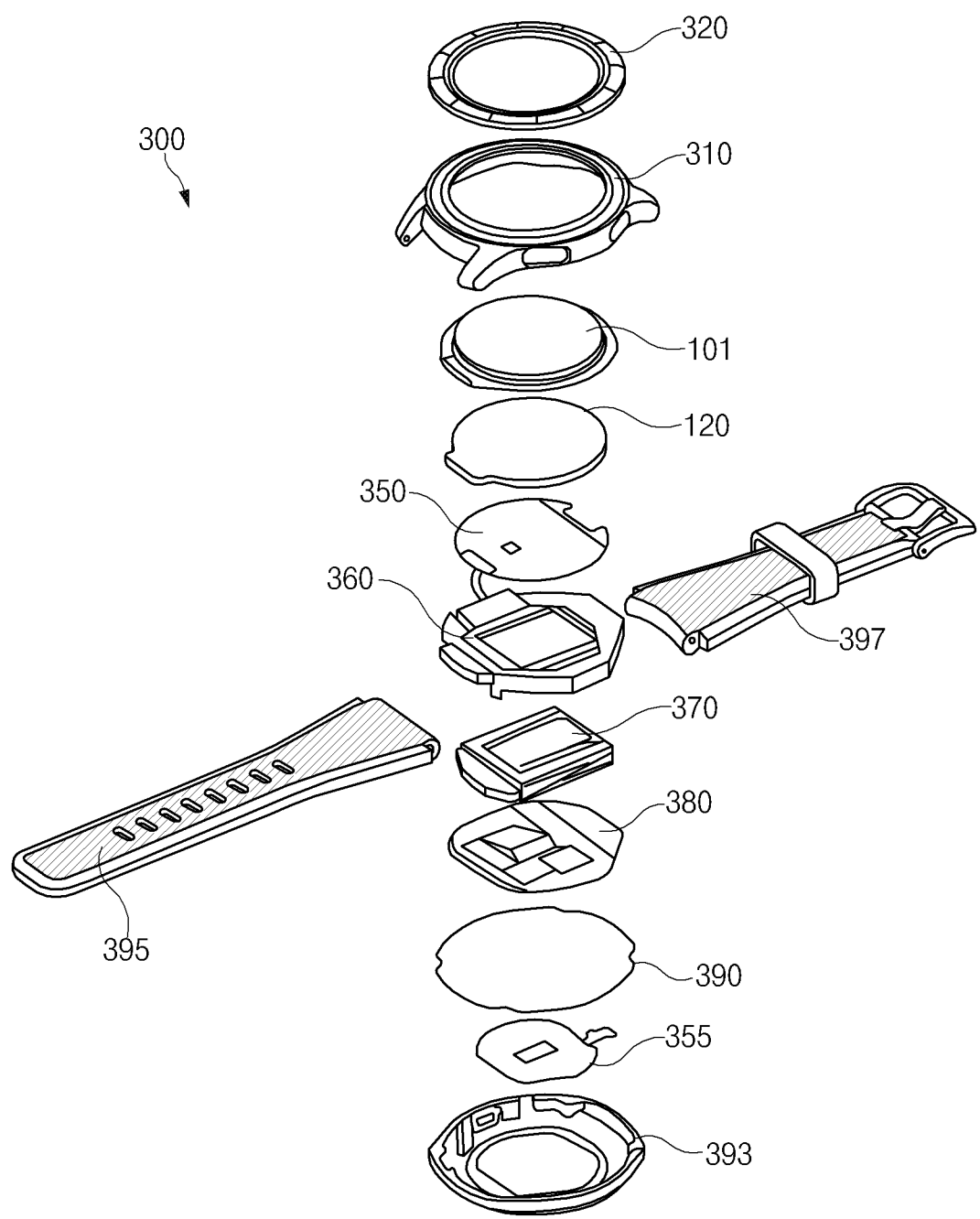
FIG. 3 is an exploded perspective view of the electronic device of FIG. 1 according to an embodiment of the disclosure.

FIG. 3 is an exploded perspective view of the electronic device of FIG. 1 according to an embodiment of the disclosure.

Referring to FIG. 3, an electronic device 300 may include a side bezel structure 310, a wheel key 320, the front plate 101, the display 120, a first antenna 350, and a second antenna 355, a support member 360 (e.g., a bracket), a battery 370, a printed circuit board (PCB) 380, a sealing member 390, a back plate 393, and coupling members 395 and 397. At least one of the components of the electronic device 300 may be the same as or similar to at least one of the components of the electronic device 100 of FIG. 1 or 2, and overlapping descriptions are omitted hereinafter. The support member 360 may be disposed inside the electronic device 300 to be connected to the side bezel structure 310 or may be integrally formed with the side bezel structure 310. The support member 360 may be formed of, for example, a metal material and/or a non-metal material (e.g., polymer). The support member 360 may be coupled to the display 120 on one surface thereof and may be coupled to the PCB 380 on the other surface thereof. The PCB 380 may be equipped with a processor, memory, and/or interface. The processor may include, for example, one or more of a central processing unit, an application processor, a graphic processing unit (GPU), an application processor sensor processor, or a communication processor.

The memory may include, for example, a volatile memory or nonvolatile memory. The interface may include, for example, a high definition multimedia interface (HDMI), a USB interface, a secure digital (SD) card interface, and/or an audio interface. The interface may, for example, electrically or physically connect the electronic device 300 to an external electronic device and may include a USB connector, an SD card/multimedia card (MMC) connector, or an audio connector.

The battery 370, which is a device for supplying power to at least one component of the electronic device 300, may include, for example, a non-rechargeable primary cell, or a rechargeable secondary cell, or a fuel cell. At least a part of the battery 370 may be disposed, for example, on substantially the same plane as the PCB 380. The battery 370 may be integrally disposed inside the electronic device 100 or may be detachably disposed with the electronic device 100.

The first antenna 350 may be disposed between the display 120 and the support member 360. The first antenna 350 may include, for example, a near field communication (NFC) antenna, a wireless charging antenna, and/or a magnetic secure transmission (MST) antenna. For example, the first antenna 350 may perform short-range communication with an external device, wirelessly transmit/receive power required for charging, and transmit a magnetic-based signal including short-range communication signals or payment data. In another embodiment, an antenna structure may be formed by a part of the side bezel structure 310 and/or the support member 360 or a combination thereof.

The second antenna 355 may be disposed between the PCB 380 and the back plate 393. The second antenna 355 may include, for example, an NFC antenna, a wireless charging antenna, and/or an MST antenna. For example, the second antenna 355 may perform short-range communication with the external device, wirelessly transmit/receive power required for charging, and transmit the magnetic-based signal including short-range communication signals or payment data. In another embodiment, the antenna structure may be formed by a part of the side bezel structure 310 and/or the back plate 393 or a combination thereof.

The sealing member 390 may be disposed between the side bezel structure 310 and the back plate 393. The sealing member 390 may be configured to block moisture and foreign matter flowing into the space surrounded by the side bezel structure 310 and the back plate 393 from the outside.

Figure 4:
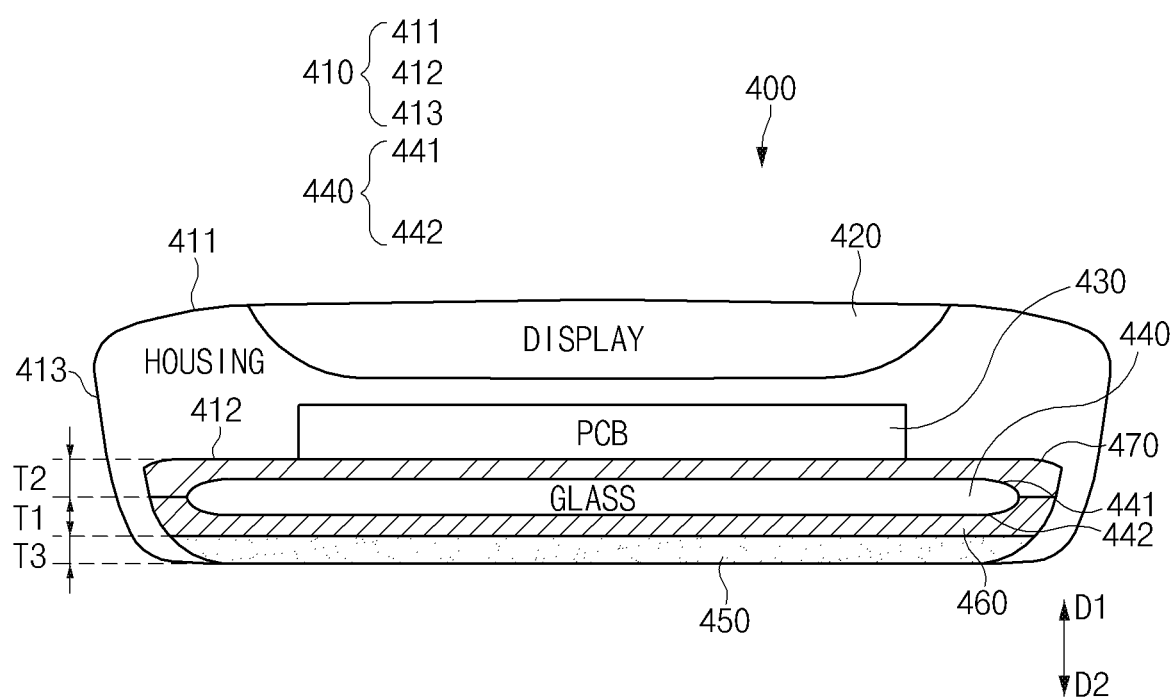
FIG. 4 is a view illustrating a housing, a display, a printed circuit board (PCB), a glass, a high-hardness member, a first conductive member, and a second conductive member of an electronic device according to an embodiment of the disclosure.

FIG. 4 is a view 400 illustrating a housing 410, a display 420, a PCB 430, a glass 440, a high-hardness member 450, a first conductive member 460, and a second conductive member 470 of an electronic device (e.g., the electronic device 100 of FIG. 1) according to an embodiment of the disclosure.

In an embodiment, the housing 410 may have a configuration substantially the same as the housing 110 of FIG. 1. The housing 410 may include a first surface 411, a second surface 412, and a third surface 413. The first surface 411 may face a first direction D1. When the electronic device 100 is a wearable electronic device, the first direction D1 may be a direction toward the outside when the user wears the electronic device 100. The second surface 412 may face a second direction D2 opposite to the first surface 411. When the electronic device 100 is a wearable electronic device, the second direction D2 may be a direction toward the user when the user wears the electronic device 100. For example, when the electronic device 100 is a smart watch, the second direction D2 may be a direction toward the user's wrist when the user wears the electronic device 100. The third surface 413 may connect the first surface 411 to the second surface 412. The third surface 413 may form a space inside the electronic device 100. The third surface 413 may be configured as at least a part of a side member of the electronic device 100. For example, when the electronic device 100 is a smart watch, the third surface 413 may be configured as a side bezel of the electronic device 100.

In an embodiment, the display 420 may be viewed in the first direction D1 through the first surface 411 of the housing 410. The display 420 may display information transmitted/received or processed by the electronic device 100 to the user. When the electronic device 100 is a wearable electronic device, the display 420 may display biometric information related to a user's body condition. For example, when the electronic device 100 is a smart watch, the display 420 is an ECG of a user, a user's heart rate, and/or a user's photo plethysmograph (PPG) measured by a sensor of the electronic device 100 (e.g., a sensor module 1776 of FIG. 17) may be displayed in a numerical and/or graphical form.

In an embodiment, the PCB 430 may be disposed in the space. The PCB 430 may include a processor (e.g., a processor 1720 of FIG. 17). The PCB 430 may control an overall operation of the electronic device 100.

In an embodiment, the glass 440 may include a fourth surface 441 and a fifth surface 442. The fourth surface 441 may cover at least a part of the second surface 412 of the housing 410. The fourth surface 441 may face the first direction D1. The fifth surface 442 may face the second direction D2.

In an embodiment, the high-hardness member 450 may be disposed on the fifth surface 442. The high-hardness member 450 may face the second direction D2. When the electronic device 100 is a wearable electronic device, the high-hardness member 450 may be in contact with the user's body when the user wears the electronic device 100. For example, when the electronic device 100 is a smart watch, the high-hardness member 450 may be in contact with the user's wrist when the user wears the electronic device 100.

In an embodiment, the high-hardness member 450 may have a hardness greater than a specified hardness. When the electronic device 100 is a wearable electronic device, the high-hardness member 450 may have excellent mechanical, chemical, and physiological characteristics for being in contact with the user's body when the user wears the electronic device 100.

In an embodiment, the high-hardness member 450 may have a mechanical strength greater than a specified strength. A surface of the high-hardness member 450 may be damaged by friction with the outside, such as a user's body, to cause a resistance to increase. A material forming the high-hardness member 450 may have a Mohs hardness (MOHS) of 5 or more to prevent the resistance of the high-hardness member 450 from increasing.

In an embodiment, the high-hardness member 450 may have chemical characteristics including corrosion resistance, temperature resistance, and/or moisture resistance that satisfy a specified condition in relation to the usability of the electronic device 100. The high-hardness member 450 may have corrosion resistance that satisfies a specified condition because the high-hardness member 450 is exposed to an external environment. For example, when the electronic device 100 is a smart watch, the high-hardness member 450 may have corrosion resistance greater than or equal to a specified value for sweat on the user's wrist. The high-hardness member 450 may have a temperature resistance that normally operates in a designated temperature range to be used in an environment of high or low temperature. For example, when the electronic device 100 is a smart watch, the high-hardness member 450 may be formed of a material capable of withstanding high temperature and/or temperature changes during four seasons in use environment. The high-hardness member 450 may have moisture resistance that normally operates in a humid environment. For example, when the electronic device 100 is a smart watch, the high-hardness member 450 may have moisture resistance against a humid environment in use and/or against sweat in the user's wrist.

In an embodiment, the high-hardness member 450 may have physiological characteristics that satisfy a specified condition. For example, when the electronic device 100 is a wearable electronic device, the high-hardness member 450 may be in contact with a user's skin for a long time to measure the user's biometric information. The high-hardness member 450 may be a material that has no stimulation to the user's skin or minimizes stimulation.

In an embodiment, the high-hardness member 450 may include at least one of an oxide-based material, a nitride-based material, and/or carbide-based material. For example, the high-hardness member 450 is a transparent material such as Indium Tin Oxide (ITO), Tin Oxide (SnO), Zinc Oxide (ZnO), and Fluorine-doped Tin Oxide (FTO) and/or an opaque material such as titanium dioxide ($TiO_2$), among oxide-based materials. As another example, the high-hardness member 450 may include materials such as chromium nitride (CrN), chromium carbon-nitride (CrCN), chromium silicon carbon nitride (CrSiCN), titanium nitride (TiN), titanium carbon nitride (TiCN), chromium boron carbon nitride (CrBCN), chromium boron silicon carbon nitride (CrBSiCN), chromium titanium carbon nitride (CrTiCN), chromium titanium silicon carbon nitride (CrTiSiCN), chromium aluminum carbon nitride (CrAlCN) and chromium aluminum silicon carbon nitride (CrAlSiCN) among the nitride-based materials. As still another example, the high-hardness member 450 may include materials such as tungsten carbide (WC) and titanium carbide (TiC) among the carbide-based materials.

In an embodiment, the first conductive member 460 may be disposed between the high-hardness member 450 and the glass 440. The first conductive member 460 may be disposed to be in contact with the fifth surface 442 of the glass 440.

In an embodiment, when the high-hardness member 450 is disposed to be in contact with the fifth surface 442 of the glass 440, the high-hardness member 450 may not satisfy conditions related to electrical conductivity specified on the fifth surface 442 of the glass 440. When the first conductive member 460 is disposed on the fifth surface 442 of the glass 440, a sheet resistance of the fifth surface 442 may decrease to satisfy the conditions related to electrical conductivity specified on the fifth surface 442 of the glass 440. For example, an electrode material constituting the first conductive member 460 may be formed on the fifth surface 442 of the glass 440 using a method such as sputtering deposition, chemical vapor deposition (CVD), and/or coating to form the first conductive member 460.

In an embodiment, the second conductive member 470 may be disposed on the fourth surface 441. The second conductive member 470 may be electrically connected to the PCB 430.

In an embodiment, the first conductive member 460 and the second conductive member 470 may each have an electrical conductivity greater than or equal to a specified electrical conductivity. The first conductive member 460 and the second conductive member 470 may each include a material capable of minimizing resistance. For example, the first conductive member 460 and the second conductive member 470 may include at least one of chromium (Cr), titanium (Ti), gold (Au), silver (Ag), graphene, carbon nanotube (CNT), or a mixture containing one or more of the above materials. The first conductive member 460 and the second conductive member 470 may be formed of substantially the same material. The first conductive member 460 and the second conductive member 470 may be integrally formed to surround the glass 440 in one process. However, the disclosure is not limited thereto, and the first conductive member 460 and the second conductive member 470 may be each formed of a material having electrical conductivity greater than or equal to a specified electrical conductivity.

In an embodiment, the first conductive member 460 may have a first thickness T1. The second conductive member 470 may have a second thickness T2. The high-hardness member 450 may have a third thickness T3. The first thickness T1 may be 1 micrometer (μm) or more and 100 μm or less. When the first thickness T1 exceeds 100 μm, mechanical hardness characteristics of the high-hardness member 450 might not satisfy specification conditions related to the mechanical characteristics of the electronic device 100. When the first thickness T1 is less than 1 μm, the resistance may be increased due to the high-hardness member 450 and not satisfy the specification conditions related to the electrical characteristics of the electronic device 100.

Figure 5:
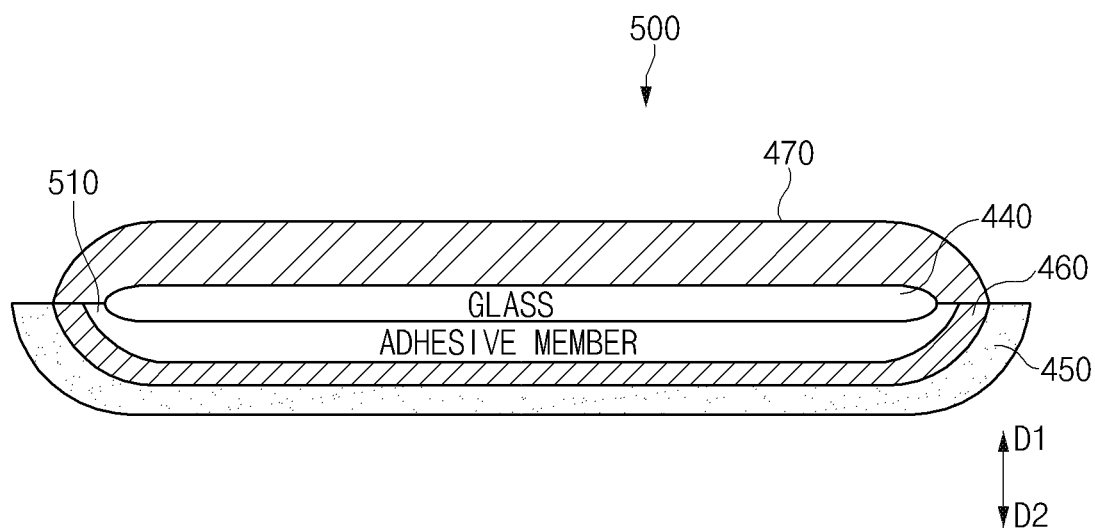
FIG. 5 is a diagram illustrating a part of an electronic device including an adhesive member according to an embodiment of the disclosure.

FIG. 5 is a diagram 500 illustrating a part of an electronic device (e.g., the electronic device 100 of FIG. 1) including an adhesive member 510 according to an embodiment of the disclosure.

In an embodiment, the adhesive member 510 may be disposed between the glass 440 and the first conductive member 460. The adhesive member 510 may be formed by depositing or coating an adhesive material on the surface of the glass 440. For example, the adhesive member 510 may be formed by depositing or coating silicon dioxide ($SiO2$) on the fifth surface 442 of the glass 440. The adhesive member 510 may increase bonding energy of the surface of the first conductive member 460 and/or the surface of the glass 440. The adhesive member 510 may increase adhesion between the first conductive member 460 and the glass 440. The adhesive member 510 may prevent the first conductive member 460 from being detached from the glass 440 while the user uses the electronic device 100.

Figure 6:
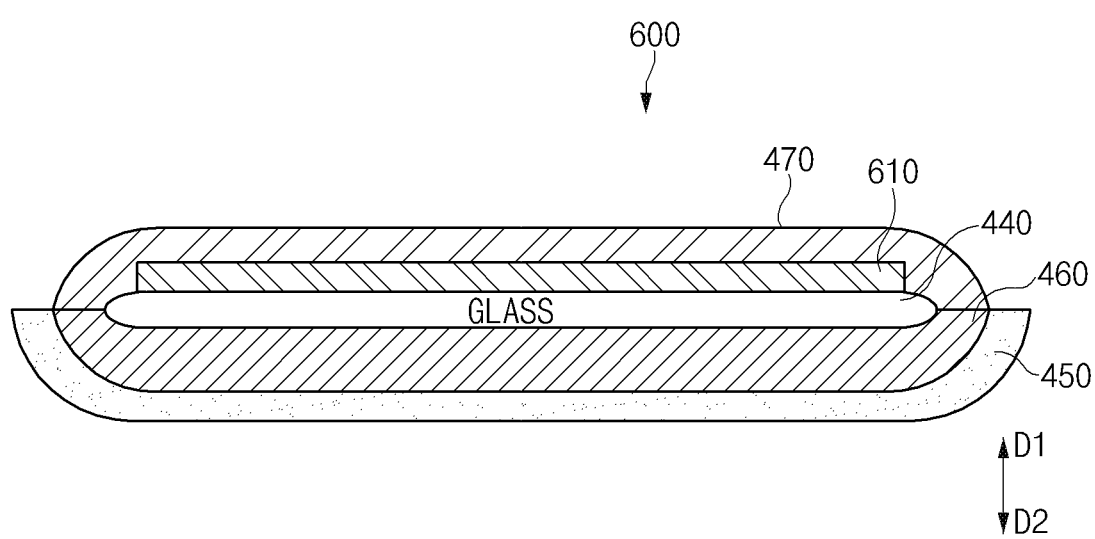
FIG. 6 is a diagram illustrating a part of an electronic device including a light blocking member according to an embodiment of the disclosure.

FIG. 6 is a diagram 600 illustrating a part of an electronic device (e.g., the electronic device 100 of FIG. 1) including a light blocking member 610 according to an embodiment of the disclosure.

In an embodiment, the light blocking member 610 may be disposed between the glass 440 and the second conductive member 470. The light blocking member 610 may include black carbon. The light blocking member 610 may be formed on the fourth surface 441 of the glass 440 in a printing method. The light blocking member 610 may be disposed to allow the PCB 430 disposed below the fourth surface 441 not to be recognized from the outside when viewed in the first direction D1.

Figure 7A:
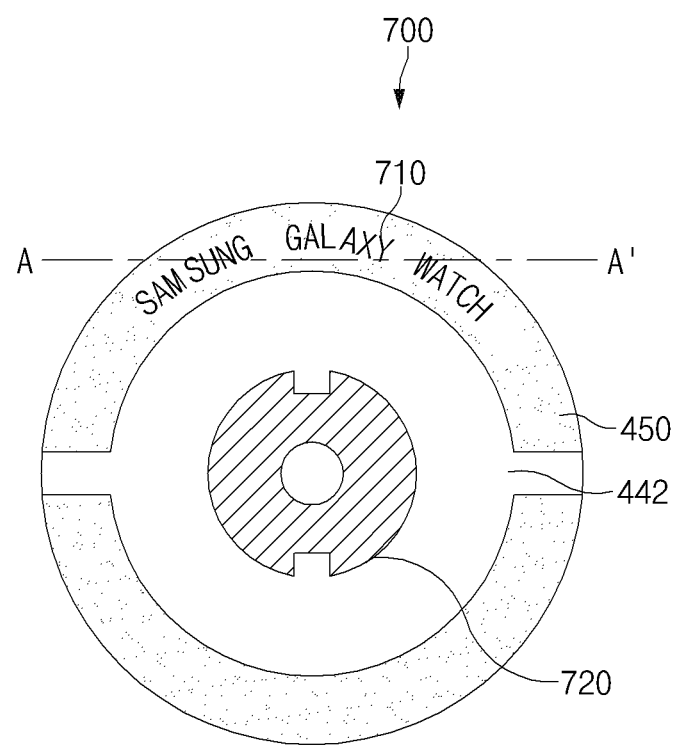
FIG. 7A is a view of a fifth surface of a glass of an electronic device including an identifier viewed in a first direction according to an embodiment of the disclosure.
Figure 7B:
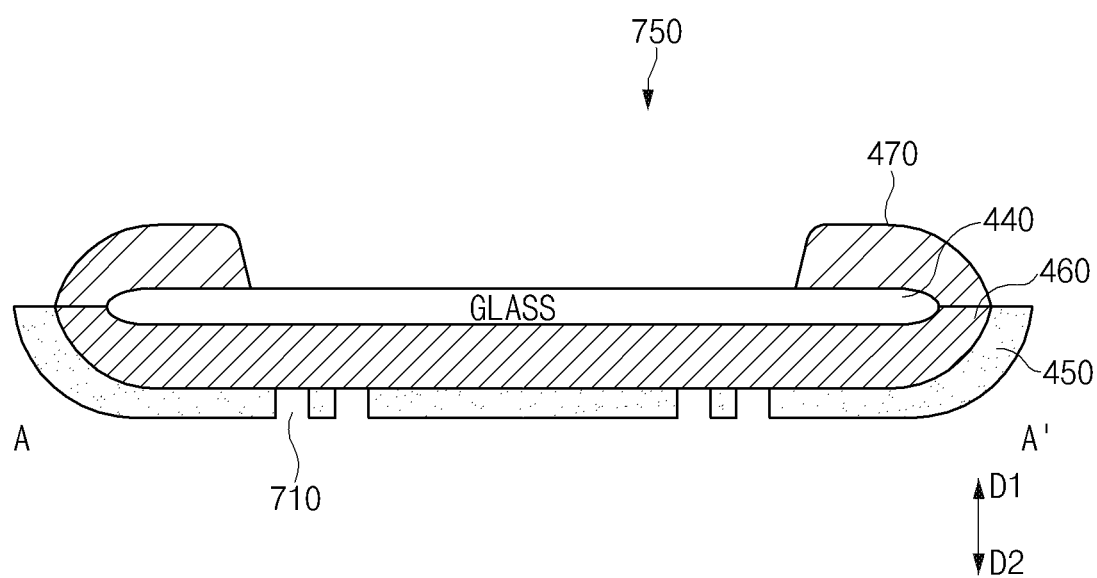
FIG. 7B is a view illustrating a part of an electronic device including an identifier according to an embodiment of the disclosure.

FIG. 7A is a view 700 of a fifth surface (e.g., the fifth surface 442 of FIG. 4) of a glass (e.g., the glass 440 of FIG. 4) of an electronic device (e.g., the electronic device 100 of FIG. 1) including an identifier 710 viewed in the first direction D1 according to an embodiment of the disclosure. FIG. 7B is a view 750 illustrating a part of an electronic device including the identifier 710 according to an embodiment of the disclosure. FIG. 7B is a cross-sectional view taken along line A-A' in FIG. 7A.

In an embodiment, the identifier 710 may be formed on the high-hardness member 450. The identifier 710 may be formed to be engraved to expose at least a part of the first conductive member 460. The identifier 710 may be formed by cutting at least a part of the high-hardness member 450. For example, the high-hardness member 450 may be cut to form the identifier 710 for inserting a logo such as "SAMSUNG GALAXY WATCH" when the fifth surface 442 is viewed in the first direction D1. The first conductive member 460 may be exposed at a portion where the high-hardness member 450 is cut to form the identifier 710. The user may easily recognize the identifier 710 because color and/or texture of the first conductive member 460 is different from color and/or texture of the high-hardness member 450.

In an embodiment, the second conductive member 470 may be disposed not to overlap with the identifier 710 in the first direction D1 and/or the second direction D2. The high-hardness member 450 may be cut by applying a perforation means such as a laser on the high-hardness member 450 to form the engraved identifier 710. When applying the perforation means on the high-hardness member 450, the first conductive member 460 and/or the second conductive member 470 disposed in the first direction D1 and/or the second direction D2 may be affected by the perforation means. When the second conductive member 470 does not overlap with the identifier 710 in the first direction D1 and/or the second direction D2, the second conductive member 470 may not be affected by the perforation means during forming the identifier 710.

In an embodiment, the second conductive member 470 may have a different area from that of the first conductive member 460. For example, the first conductive member 460 may be formed entirely on the fifth surface 442 to insert the high-hardness member 450 and the identifier 710. The second conductive member 470 may be formed on a part of the fourth surface 441 to have a smaller area than the first conductive member 460 on which the identifier 710 is formed. Accordingly, the second conductive member 470 may not be affected by the perforation means when forming the identifier 710.

In an embodiment, a sensor 720 may be disposed on the fifth surface 442. The sensor 720 may be disposed at a center of the fifth surface 442. The sensor 720 may acquire biometric information of the user. For example, when the electronic device 100 is a smart watch, the sensor 720 may measure the user's electrocardiogram and/or heart rate.

Figure 8:
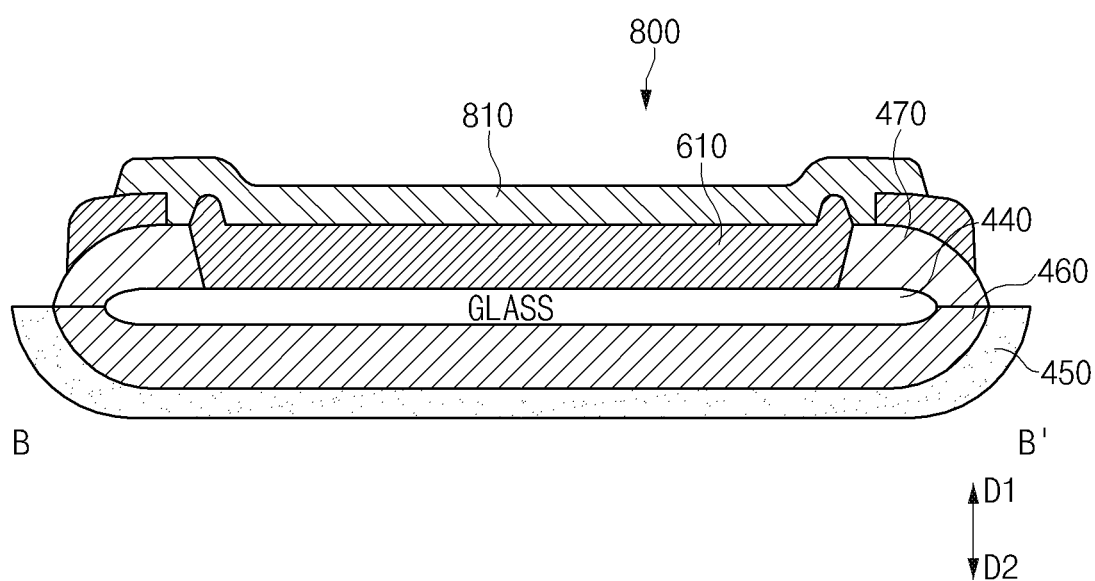
FIG. 8 is a view illustrating a part of an electronic device including a third conductive member according to an embodiment of the disclosure.

FIG. 8 is a diagram 800 illustrating a part of an electronic device (e.g., the electronic device 100 of FIG. 1) including a third conductive member 810 according to an embodiment of the disclosure. FIG. 8 is a cross-sectional view taken along line B-B' of FIG. 12.

In an embodiment, the third conductive member 810 may connect the second conductive member 470 to the PCB 430. The third conductive member 810 may be disposed on a fourth surface (e.g., the fourth surface 441 of FIG. 4) of the glass 440 when the second conductive member 470 has a smaller area than that of the first conductive member 460. The third conductive member 810 may be disposed to overlap the PCB 430 in the first direction D1 and/or the second direction D2. For example, when the light blocking member 610 is disposed to cause the second conductive member 470 to have the smaller area than that of the first conductive member 460, the third conductive member 810 may be disposed to cover at least a part of the second conductive member 470 and the light blocking member 610. As another example, when the identifier (e.g., the identifier 710 of FIG. 7A) is disposed to cause the second conductive member 470 to have the smaller area than that of the first conductive member 460, the third conductive member 810 may be disposed to extend to an area overlapped with the identifier 710 in the first direction D1 and/or the second direction D2.

In an embodiment, the third conductive member 810 may be formed after the second conductive member 470, the light blocking member 610, and/or the identifier 710 are formed. The third conductive member 810 may be made of a paste and/or ink type material. For example, the third conductive member 810 may be made of at least one of silver paste, conductive carbon paste, conductive film, and conductive polymer. The third conductive member 810 may be formed by a method such as printing, spraying, coating, and/or attaching. For example, the third conductive member 810 may be formed by printing silver paste.

Figure 9:
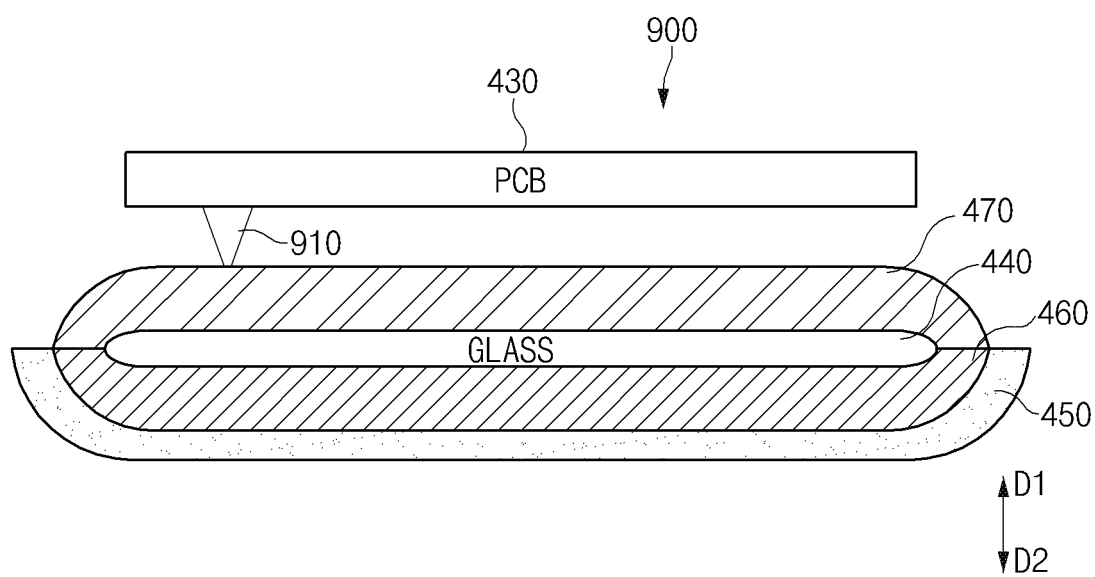
FIG. 9 is a view illustrating a part of an electronic device including a connector according to an embodiment of the disclosure.

FIG. 9 is a view 900 illustrating a part of an electronic device (e.g., the electronic device 100 of FIG. 1) including a connector 910 according to an embodiment of the disclosure.

In an embodiment, the connector 910 may be formed from the second conductive member 470 in the first direction D1. The connector 910 may connect the second conductive member 470 to the PCB 430. The connector 910 may connect the second conductive member 470 to the circuit connection terminal of the PCB 430. The connector 910 may be disposed to connect the second conductive member 470 to a circuit for obtaining biometric information disposed on the PCB 430. The connector 910 may have a shape such as a pogo pin, a C-clip, and/or a gasket. The connector 910 may be made of a material having lower electrical resistance than the second conductive member 470.

Figure 10:
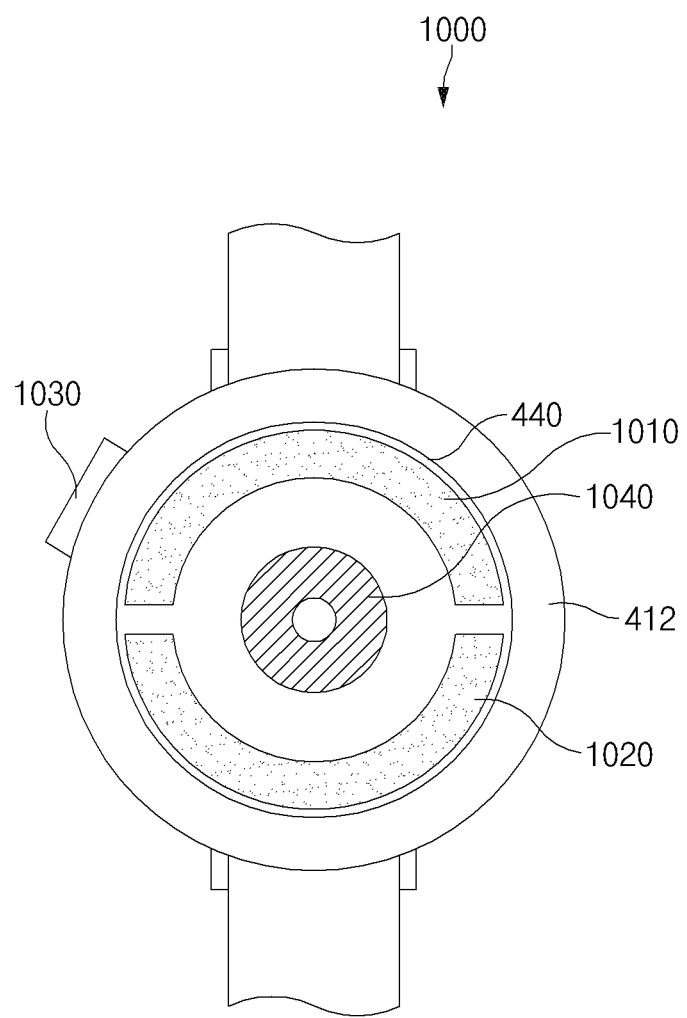
FIG. 10 is a view illustrating a second surface of a housing of an electronic device including a first electrode, a second electrode, and a third electrode according to an embodiment of the disclosure.

FIG. 10 is a view 1000 illustrating a second surface (e.g., the second surface 412 of FIG. 4) of the housing (e.g., the housing 410 of FIG. 4) of an electronic device (e.g., the electronic device 100 of FIG. 1) including a first electrode 1010, a second electrode 1020, and a third electrode 1030, according to an embodiment of the disclosure.

In an embodiment, the first electrode 1010 may be disposed on the glass 440. The first electrode 1010 may be disposed on at least a part of an edge region excluding a central region of the glass 440. The first electrode 1010 may include a high-hardness member (e.g., the high-hardness member 450 of FIG. 4) disposed on a fifth surface (e.g., the fifth surface 442 of FIG. 4) of the glass 440, a first conductive member (e.g., the first conductive member 460 in FIG. 4) disposed between the high-hardness member 450 and the glass 440, and a second conductive member (e.g., the second conductive member 470 of FIG. 4) disposed on a fourth surface (e.g., the fourth surface 441 in FIG. 4) to be electrically connected to the PCB (e.g., the PCB 430 of FIG. 4).

In an embodiment, the first electrode 1010 may obtain a voltage depending on user's biometric information. The first electrode 1010 may measure biometric information of the user. For example, when the electronic device 100 is a smart watch, the first electrode 1010 may measure the user's electrocardiogram (ECG) and/or heart rate. The first electrode 1010 may measure the heartbeat of the user while viewing the heart. For example, the first electrode 1010 may sense a micro current generated when the user's heart beats. The first electrode 1010 may have a first voltage. The first voltage may have a magnitude and/or waveform that varies depending on the user's biometric information. For example, when the electronic device 100 is a smart watch, the first voltage may have a magnitude and/or waveform responding to a voltage depending on a change in the user's electrocardiogram.

In an embodiment, the second electrode 1020 may be disposed on a region, except for a region where the first electrode 1010 is disposed, among the edge region of the glass 440. The second electrode 1020 may be disposed on the glass 440 to be adjacent to the first electrode 1010. The second electrode 1020 may have a ground voltage. The second electrode 1020 may include the high-hardness member 450, the first conductive member 460, and the second conductive member 470. The second electrode 1020 may have a layer structure substantially the same as that of the first electrode 1010.

In an embodiment, the third electrode 1030 may be disposed to be spaced apart from the first electrode 1010 and the second electrode 1020. The third electrode 1030 may have a second voltage having a polarity opposite to that of the first voltage, based on the ground voltage.

In an embodiment, a sensor 1040 may be disposed at the central region of the glass 440. The sensor 1040 may acquire biometric information of the user. The biometric information of the user acquired by the sensor 1040 may be different from the biometric information of the user measured by the first electrode 1010. For example, when the electronic device 100 is a smart watch, the sensor 1040 may acquire a user's heart rate.

In an embodiment, the sensor 1040 may measure bio-information based on blood flow flowing through a user's blood vessel. For example, the sensor 1040 may use a light reflected after being emitted toward the user's blood vessel to measure photo plethysmograph (PPG), blood pressure, and/or oxygen saturation of the user. The sensor 1040 may acquire raw data related to biometric information of the user different from the first electrode 1010. However, the disclosure is not limited thereto, and the sensor 1040 may acquire and/or define some common biometric information (e.g., a user's heart rate) with the first electrode 1010.

Figure 11:
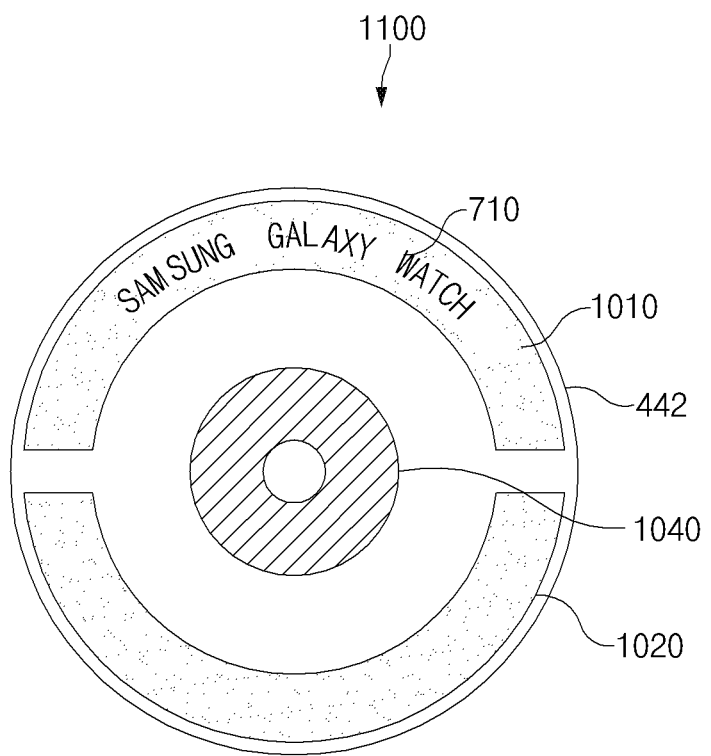
FIG. 11 is a view of a fifth surface of a glass of an electronic device including a first electrode and a second electrode, viewed in a first direction according to an embodiment of the disclosure.

FIG. 11 is view 1100 of a fifth surface (e.g., the fifth surface 442 of FIG. 4) of a glass (e.g., the glass 440 of FIG. 4) of an electronic device (e.g., the electronic device 100 of FIG. 1) including the first electrode 1010 and the second electrode 1020, viewed in the first direction D1 according to an embodiment of the disclosure.

In an embodiment, the first electrode 1010 may be disposed on at least a part of the fifth surface 442. The second electrode 1020 may be disposed to be spaced apart from the first electrode 1010 on the fifth surface 442.

In an embodiment, the first electrode 1010 may measure electrocardiogram of a wearer wearing the electronic device 100. For example, the electronic device 100 may compare the first voltage responding to the electrocardiogram measured by the first electrode 1010 with the ground voltage of the second electrode 1020 to calculate a waveform over time.

In an embodiment, the identifier 710 may be disposed on the first electrode 1010. At least a part of the high-hardness member (e.g., the high-hardness member 450 of FIG. 4) of the first electrode 1010 may be etched and the first conductive member (e.g., the first conductive member 460 of FIG. 4) of the first electrode 1010 may be exposed to form the identifier 710. For example, the identifier 710 may be a logo such as "SAMSUNG GALAXY WATCH."

In an embodiment, the sensor 1040 may be disposed in the central region of the fifth surface 442. The sensor 1040 may measure the heart rate of the wearer.

In an embodiment, the first electrode 1010 may be electrically connected to the user's skin to obtain the user's electrocardiogram. The second electrode 1020 may maintain a state of a ground voltage.

In an embodiment, a resistance of the first electrode 1010 may be between 1 ohm ($\Omega$) and 1 kiloohm (k$\Omega$). A resistance of the second electrode 1020 may be between 1 $\Omega$ and 1 k$\Omega$. Accordingly, an internal resistance that is a resistance between the fourth surface 441 and the fifth surface 442 of the glass 440 may be between 1 $\Omega$ and 1 k$\Omega$.

In an embodiment, the first electrode 1010 and the second electrode 1020 may be electrically separated. For example, a resistance between the first electrode 1010 and the second electrode 1020 may be between 1 gigaohm (G$\Omega$) and 10 G$\Omega$. Accordingly, the first electrode 1010 may have a first voltage having a waveform responding to a result of measuring the user's electrocardiogram and the second electrode 1020 may have a ground voltage.

Figure 12:
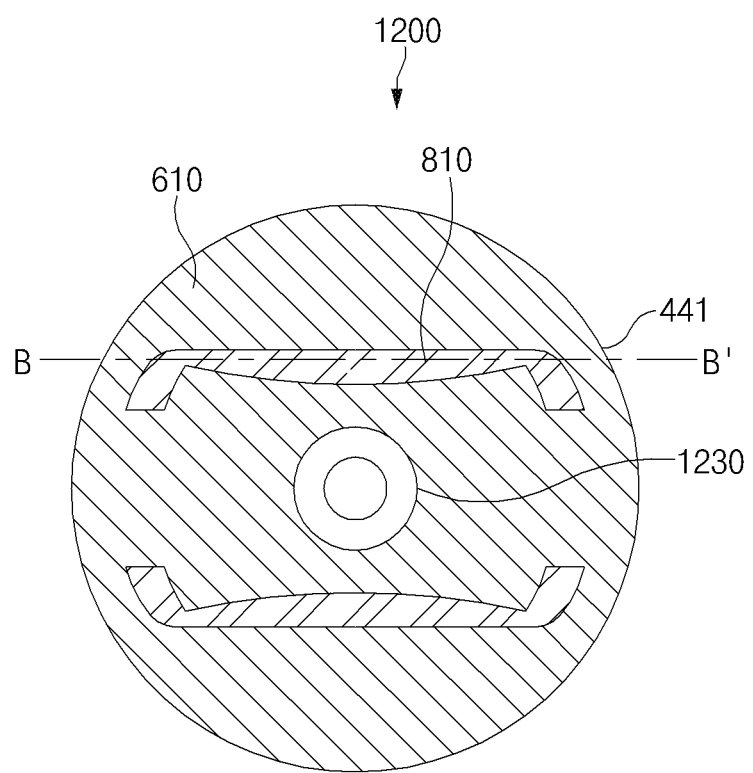
FIG. 12 is a view of a fourth surface of a glass of an electronic device including a first electrode and a second electrode, viewed in a second direction according to an embodiment of the disclosure.

FIG. 12 is a view 1200 of a fourth surface (e.g., the fourth surface 441 of FIG. 4) of a glass (e.g., the glass 440 of FIG. 4) of an electronic device (e.g., the electronic device of FIG. 1) including a first electrode (e.g., the first electrode 1010 of FIG. 10) and a second electrode (e.g., the second electrode 1020 of FIG. 10) viewed in the second direction D2 according to an embodiment of the disclosure.

In an embodiment, the second conductive member (e.g., the second conductive member 470 in FIG. 4) may be disposed not to overlap with an identifier (e.g., the identifier 710 in FIG. 11) in a first direction (e.g., the first direction D1 of FIG. 4) and/or a second direction (e.g., the second direction D2 of FIG. 4). The light blocking member 610 may be covered on the fourth surface 441 including the region where the second conductive member 470 is disposed. For example, the light blocking member 610 may be disposed on a region, except for the first electrode 1010 and the second electrode 1020.

In an embodiment, the third conductive member 810, which connects the second conductive member 470 to the PCB 430 may further included. The second conductive member 470 may be disposed not to overlap with the identifier 710 in the first direction D1 and/or the second direction D2. The third conductive member 810 may be formed to connect at least a part of the second conductive member 470 to a region where the light blocking member 610 is not disposed. The third conductive member 810 may be a silver paste. The third conductive member 810 may be exposed in at least a part of the fourth surface 441 to form at least a part of the first electrode 1010 and the second electrode 1020.

In an embodiment, the third conductive member 810 may include a third terminal and a fourth terminal. The third terminal may connect the third conductive member 810 constituting the first electrode 1010 to the PCB 430. The fourth terminal may connect the third conductive member 810 constituting the second electrode 1020 to the PCB 430.

In an embodiment, a sensor 1230 may be disposed not to overlap with the first electrode 1010 and the second electrode 1020. For example, the sensor 1230 may be disposed in the central region of the fourth surface 441 not to overlap with the third conductive member 810 constituting the first electrode 1010 and the second electrode 1020. The sensor 1230 may measure a photo plethysmograph (PPG) of a wearer wearing the electronic device 100.

Figure 13:
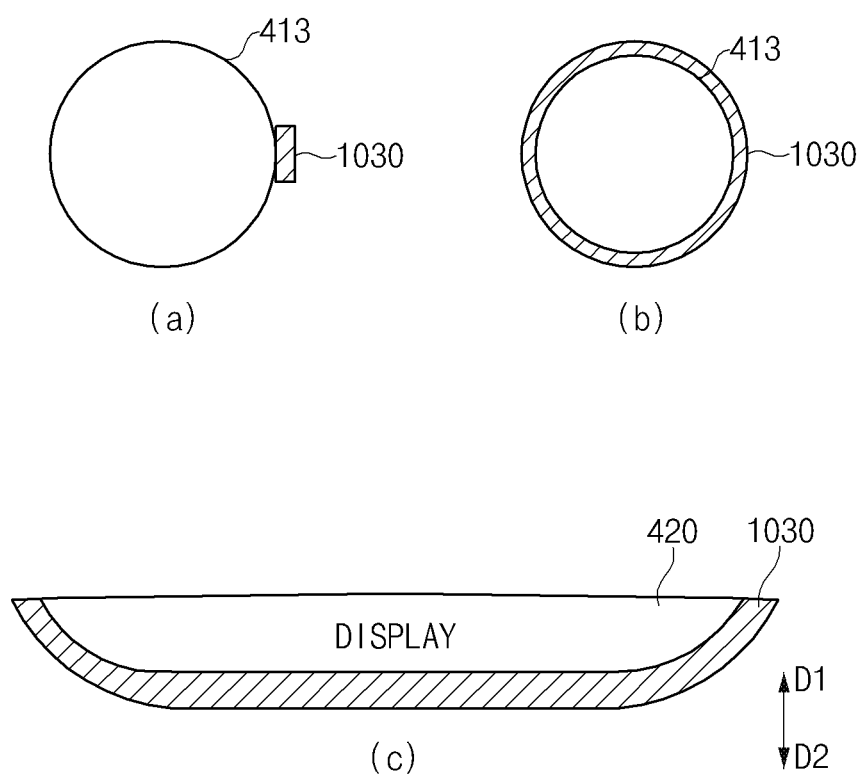
FIG. 13 is a view illustrating a third electrode according to an embodiment of the disclosure.

FIG. 13 is a view illustrating the third electrode 1030 according to an embodiment of the disclosure.

In an embodiment, as illustrated in (a), the third electrode 1030 may be a button formed on at least a part of the third surface 413 of a housing (e.g., the housing 410 of FIG. 4). For example, the third electrode 1030 may be a side key. The third electrode 1030 may measure biometric information of the user at a portion opposite to a first electrode (e.g., the first electrode 1010 of FIG. 10). The third electrode 1030 may have a second voltage having opposite polarity to the first voltage.

In an embodiment, as illustrated in (b), the third electrode 1030 may be a ring formed using a conductive material constituting at least a part of the third surface 413 of the housing 410. For example, the third electrode 1030 may be a side bezel.

In an embodiment, as illustrated in (c), the third electrode 1030 may be a transparent electrode constituting at least a part of the display 420. In the case of (c), the side of the display 420 is illustrated as viewed from the side of the electronic device (e.g., the electronic device 100 of FIG. 1). The third electrode 1030 may be disposed on a surface facing the second direction D2 of the display 420. For example, the third electrode 1030 may be a top window. When the top window is used as an electrode, the third electrode 1030 may be formed using a transparent electrode such as ITO.

Figure 14:
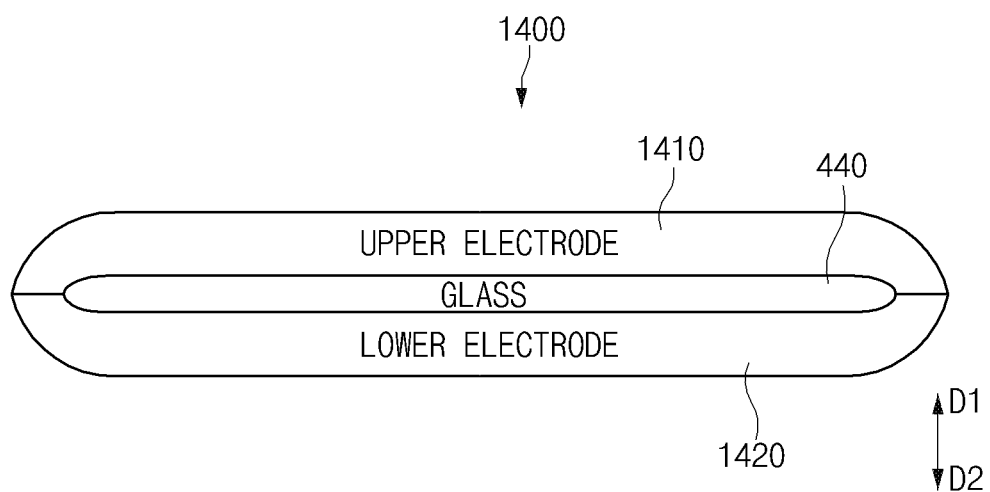
FIG. 14 is a view illustrating an electronic device including an upper electrode and a lower electrode according to an embodiment of the disclosure.

FIG. 14 is a view 1400 illustrating an electronic device (e.g., the electronic device 100 of FIG. 1) including an upper electrode 1410 and a lower electrode 1420 according to an embodiment of the disclosure.

In an embodiment, the lower electrode 1420 may be disposed on a fifth surface (e.g., the fifth surface 442 of FIG. 4) of the glass 440. The lower electrode 1420 may be in contact with the user's body.

In an embodiment, the upper electrode 1410 may be disposed to be in contact with the lower electrode 1420 at a boundary line that is in contact with a housing (e.g., the housing 410 of FIG. 4). The upper electrode 1410 may be disposed on a fourth surface (e.g., the fourth surface 441 of FIG. 4) of the glass 440. The upper electrode 1410 may be electrically connected to a PCB (e.g., the PCB 430 of FIG. 4).

In an embodiment, the upper electrode 1410 and the lower electrode 1420 may constitute a first electrode (e.g., the first electrode 1010 of FIG. 10) and a second electrode (e.g., the second electrode 1020 of FIG. 10). The first electrode 1010 may include the lower electrode 1420 and the upper electrode 1410 to be disposed to surround at least a part of the glass 440. The second electrode 1020 may be formed with the lower electrode 1420 and the upper electrode 1410 and may be separated from the first electrode 1010 to be disposed to surround the rest of the glass 440.

In an embodiment, a third electrode (e.g., the third electrode 1030 of FIG. 13) may be separated from the first electrode 1010 and the second electrode 1020. The third electrode 1030 may be made of the same material as the upper electrode 1410.

In an embodiment, an internal resistance between the lower electrode 1420 and the upper electrode 1410 may be between 1Ω and 1 kΩ. The electrical resistance between the user's body and the PCB 430 may be the sum of the internal resistance and a contact impedance between the user's body and the electronic device 100. The contact impedance may be an impedance of a current path generated by an electrolyte, such as sweat on the surface of a user's skin. The contact impedance may be between 0.5 megaohm (MΩ) and 1 MΩ. The internal resistance may be set to 0.1% or less of the contact impedance to satisfy a condition specified for accurately measuring the user's biometric information. Accordingly, the internal resistance may be 1 kΩ, which is 0.1% of 1 MΩ.

In an embodiment, the upper electrode 1410 may be formed of a different material from that of the lower electrode 1420. The upper electrode 1410 may be formed in a different way from the lower electrode 1420. The upper electrode 1410 may have mechanical durability responding to a structure exposed to the outside while satisfying a condition that the internal resistance is between 1 Ω and 1 kΩ.

In an embodiment, the upper electrode 1410 may be formed of a composite layer, in which high-hardness material and a conductive material are mixed at a pressure of between 0.1 megapascals (MPa) and 1 MPa to be deposited, on the fourth surface 411. The upper electrode 1410 may have high-hardness and high conductivity simultaneously to satisfy specified conditions. A high-hardness material and a conductive material may be mixed and deposited to form the upper electrode 1410 having both high-hardness and high conductivity. As vacuum degree becomes high during deposition, the high-hardness material and conductive material may be deposited with more strong energy to increase the electrical conductivity. For example, when depositing at a pressure of between 0.1 MPa and 1 MPa, an electric field (E-field) that satisfies a specified condition may be formed inside the upper electrode 1410. As another example, when increasing a composition ratio of the conductive material to be deposited, the resistance of the upper electrode 1410 may be reduced.

Figure 15:
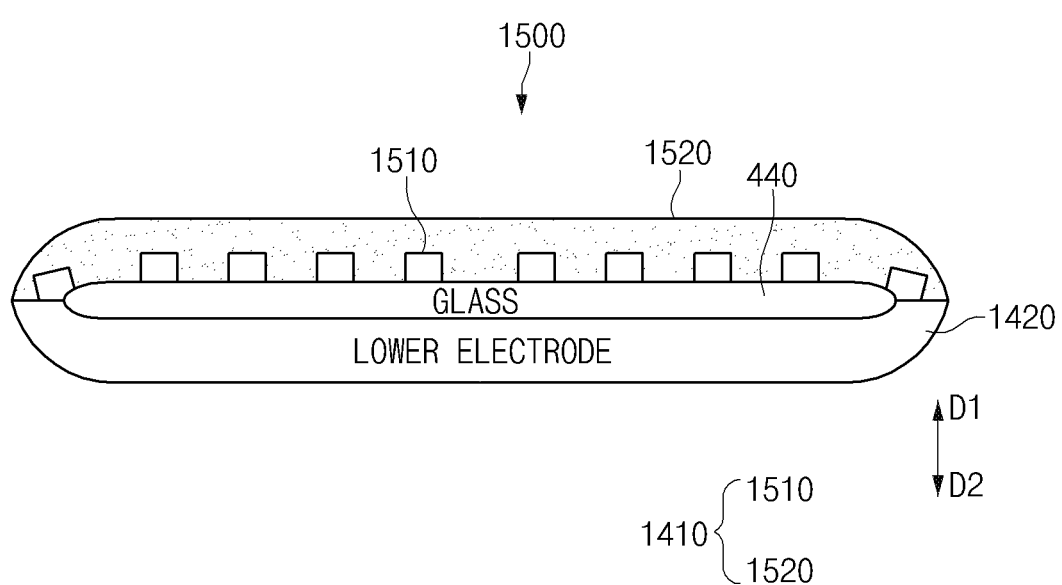
FIG. 15 is a view illustrating an upper electrode including a metal mesh and a high-hardness material according to an embodiment of the disclosure.

FIG. 15 is a view 1500 illustrating the upper electrode 1410 including a metal mesh 1510 and a high-hardness material 1520 according to an embodiment of the disclosure.

In an embodiment, the upper electrode 1410 may include the metal mesh 1510 and the high-hardness material 1520. The metal mesh 1510 may be formed on a fourth surface (e.g., the fourth surface 441 of FIG. 4). The metal mesh 1510 may be formed to cross each other along the surface of the fourth surface 441. The metal mesh 1510 may have a resistance less than or equal to a specified resistance.

In an embodiment, the high-hardness material 1520 may be formed to cover the metal mesh 1510. The high-hardness material 1520 may have a hardness greater than or equal to a specified hardness.

In an embodiment, the metal mesh 1510 may be first applied on the fourth surface 441 of the glass 440. When depositing and/or coating the high-hardness material 1520 on the fourth surface 441 on which the metal mesh 1510 is applied, the upper electrode 1410 that satisfies both high-hardness and high conductivity may be formed.

Figure 16:
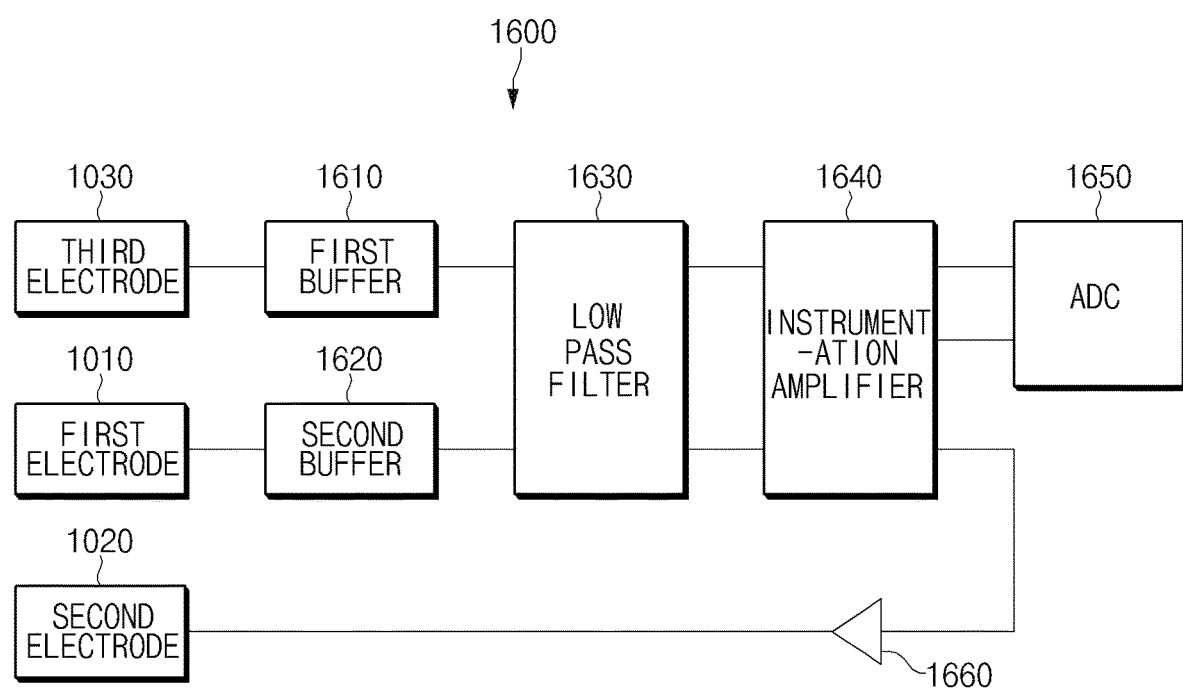
FIG. 16 is a circuit diagram of an electronic device according to an embodiment of the disclosure.

FIG. 16 is a circuit diagram 1600 of an electronic device (e.g., the electronic device 100 of FIG. 1) according to an embodiment of the disclosure.

In an embodiment, the electronic device 100 includes the first electrode 1010, the second electrode 1020, the third electrode 1030, a first buffer 1610, a second buffer 1620, and a low pass filter (LPF) 1630, an instrumentation amplifier (INA) 1640, an analog to digital converter (ADC) 1650, and/or a voltage retention unit 1660 may be included.

In an embodiment, the first electrode 1010 may acquire a first voltage that is a waveform related to the user's biometric information. For example, the first electrode 1010 may acquire a waveform measuring a user's ECG as the first voltage. The second electrode 1020 may maintain a ground voltage. The third electrode 1030 may obtain a second voltage having a polarity opposite to the first voltage.

In an embodiment, the first buffer 1610 may store or selectively delay the second voltage obtained by the third electrode 1030 to transfer the second voltage to the LPF 1630. The second buffer 1620 may store or selectively delay the first voltage obtained by the first electrode 1010 and transfer the first voltage to the LPF 1630.

In an embodiment, the LPF 1630 may receive the first voltage and/or second voltage from the first buffer 1610 and the second buffer 1620. The LPF 1630 may remove high-frequency noise mixed with the first voltage and/or second voltage. The LPF 1630 may transfer the noise-removed first voltage and/or second voltage to the INA 1640.

In an embodiment, the INA 1640 may receive the first voltage and/or the second voltage where the noise is removed from the LPF 1630. The INA 1640 may amplify the received first voltage and/or second voltage. The INA 1640 may transmit the amplified first voltage and/or second voltage to the ADC 1650.

In an embodiment, the ADC 1650 may receive the amplified first voltage and/or second voltage from the INA 1640. The ADC 1650 may convert the amplified first voltage and/or second voltage into digital data. For example, when the first voltage and/or the second voltage are waveforms measuring the user's electrocardiogram, the ADC 1650 may convert the first voltage and/or the second voltage into ECG measurement data. The ADC 1650 may transfer data converted to a digital format to a processor (e.g., the processor 1720 of FIG. 17).

In an embodiment, the voltage retention unit 1660 may be disposed between the second electrode 1020 and the INA 1640. The voltage retention unit 1660 may control the second electrode 1020 to maintain the ground voltage. The voltage retention unit 1660 may be connected to a portion (not illustrated) that maintains the ground voltage in the INA 1640 (e.g., a central portion of a resistor connecting between input terminals receiving the first voltage and the second voltage).

Figure 17:
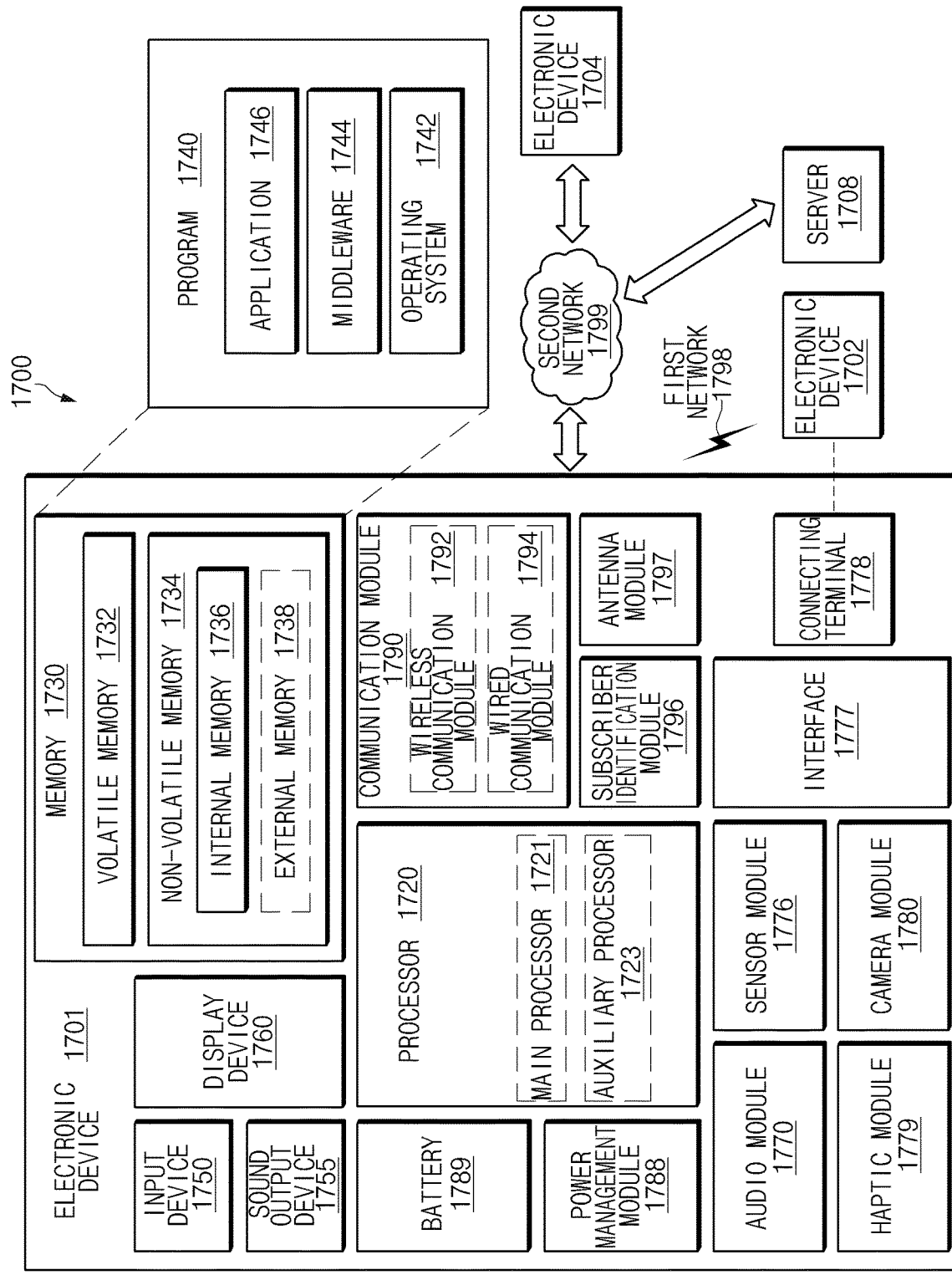
FIG. 17 is a block diagram illustrating an electronic device in a network environment according to van embodiment of the disclosure.\

FIG. 17 is a block diagram illustrating an electronic device 1701 in a network environment 1700 according to an embodiment of the disclosure.

Referring to FIG. 17, the electronic device 1701 in the network environment 1700 may communicate with an electronic device 1702 via a first network 1798 (e.g., a short-range wireless communication network), or an electronic device 1704 or a server 1708 via a second network 1799 (e.g., a long-range wireless communication network). According to an embodiment, the electronic device 1701 may communicate with the electronic device 1704 via the server 1708. According to an embodiment, the electronic device 1701 may include a processor 1720, memory 1730, an input device 1750, a sound output device 1755, a display device 1760, an audio module 1770, a sensor module 1776, an interface 1777, a haptic module 1779, a camera module 1780, a power management module 1788, a battery 1789, a communication module 1790, a subscriber identification module (SIM) 1796, or an antenna module 1797. In some embodiments, at least one (e.g., the display device 1760 or the camera module 1780) of the components may be omitted from the electronic device 1701, or one or more other components may be added in the electronic device 1701. In some embodiments, some of the components may be implemented as single integrated circuitry. For example, the sensor module 1776 (e.g., a fingerprint sensor, an iris sensor, or an illuminance sensor) may be implemented as embedded in the display device 1760 (e.g., a display).

The processor 1720 may execute, for example, software (e.g., a program 1740) to control at least one other component (e.g., a hardware or software component) of the electronic device 1701 coupled with the processor 1720, and may perform various data processing or computation. According to one embodiment, as at least part of the data processing or computation, the processor 1720 may load a command or data received from another component (e.g., the sensor module 1776 or the communication module 1790) in volatile memory 1732, process the command or the data stored in the volatile memory 1732, and store resulting data in non-volatile memory 1734. According to an embodiment, the processor 1720 may include a main processor 1721 (e.g., a central processing unit (CPU) or an application processor (AP)), and an auxiliary processor 1723 (e.g., a graphics processing unit (GPU), an image signal processor (ISP), a sensor hub processor, or a communication processor (CP)) that is operable independently from, or in conjunction with, the main processor 1721. Additionally or alternatively, the auxiliary processor 1723 may be adapted to consume less power than the main processor 1721, or to be specific to a specified function. The auxiliary processor 1723 may be implemented as separate from, or as part of the main processor 1721.

The auxiliary processor 1723 may control at least some of functions or states related to at least one component (e.g., the display device 1760, the sensor module 1776, or the communication module 1790) among the components of the electronic device 1701, instead of the main processor 1721 while the main processor 1721 is in an inactive (e.g., sleep) state, or together with the main processor 1721 while the main processor 1721 is in an active state (e.g., executing an application). According to an embodiment, the auxiliary processor 1723 (e.g., an image signal processor or a communication processor) may be implemented as part of another component (e.g., the camera module 1780 or the communication module 1790) functionally related to the auxiliary processor 1723.

The memory 1730 may store various data used by at least one component (e.g., the processor 1720 or the sensor module 1776) of the electronic device 1701. The various data may include, for example, software (e.g., the program 1740) and input data or output data for a command related thereto. The memory 1730 may include the volatile memory 1732 or the non-volatile memory 1734.

The program 1740 may be stored in the memory 1730 as software, and may include, for example, an operating system (OS) 1742, middleware 1744, or an application 1746.

The input device 1750 may receive a command or data to be used by another component (e.g., the processor 1720) of the electronic device 1701, from the outside (e.g., a user) of the electronic device 1701. The input device 1750 may include, for example, a microphone, a mouse, a keyboard, or a digital pen (e.g., a stylus pen).

The sound output device 1755 may output sound signals to the outside of the electronic device 1701. The sound output device 1755 may include, for example, a speaker or a receiver. The speaker may be used for general purposes, such as playing multimedia or playing record, and the receiver may be used for an incoming call. According to an embodiment, the receiver may be implemented as separate from, or as part of the speaker.

The display device 1760 may visually provide information to the outside (e.g., a user) of the electronic device 1701. The display device 1760 may include, for example, a display, a hologram device, or a projector and control circuitry to control a corresponding one of the display, hologram device, and projector. According to an embodiment, the display device 1760 may include touch circuitry adapted to detect a touch, or sensor circuitry (e.g., a pressure sensor) adapted to measure the intensity of force incurred by the touch.

The audio module 1770 may convert a sound into an electrical signal and vice versa. According to an embodiment, the audio module 1770 may obtain the sound via the input device 1750, or output the sound via the sound output device 1755 or a headphone of an external electronic device (e.g., an electronic device 1702) directly (e.g., wiredly) or wirelessly coupled with the electronic device 1701.

The sensor module 1776 may detect an operational state (e.g., power or temperature) of the electronic device 1701 or an environmental state (e.g., a state of a user) external to the electronic device 1701, and then generate an electrical signal or data value corresponding to the detected state. According to an embodiment, the sensor module 1776 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 1777 may support one or more specified protocols to be used for the electronic device 1701 to be coupled with the external electronic device (e.g., the electronic device 1702) directly (e.g., wiredly) or wirelessly. According to an embodiment, the interface 1777 may include, for example, a high definition multimedia interface (HDMI), a USB interface, a secure digital (SD) card interface, or an audio interface.

A connecting terminal 1778 may include a connector via which the electronic device 1701 may be physically connected with the external electronic device (e.g., the electronic device 1702). According to an embodiment, the connecting terminal 1778 may include, for example, a HDMI connector, a USB connector, a SD card connector, or an audio connector (e.g., a headphone connector).

The haptic module 1779 may convert an electrical signal into a mechanical stimulus (e.g., a vibration or a movement) or electrical stimulus which may be recognized by a user via his tactile sensation or kinesthetic sensation. According to an embodiment, the haptic module 1779 may include, for example, a motor, a piezoelectric element, or an electric stimulator.

The camera module 1780 may capture a still image or moving images. According to an embodiment, the camera module 1780 may include one or more lenses, image sensors, image signal processors, or flashes.

The power management module 1788 may manage power supplied to the electronic device 1701. According to one embodiment, the power management module 1788 may be implemented as at least part of, for example, a power management integrated circuit (PMIC).

The battery 1789 may supply power to at least one component of the electronic device 1701. According to an embodiment, the battery 1789 may include, for example, a primary cell which is not rechargeable, a secondary cell which is rechargeable, or a fuel cell.

The communication module 1790 may support establishing a direct (e.g., wired) communication channel or a wireless communication channel between the electronic device 1701 and the external electronic device (e.g., the electronic device 1702, the electronic device 1704, or the server 1708) and performing communication via the established communication channel. The communication module 1790 may include one or more communication processors that are operable independently from the processor 1720 (e.g., the application processor (AP)) and supports a direct (e.g., wired) communication or a wireless communication. According to an embodiment, the communication module 1790 may include a wireless communication module 1792 (e.g., a cellular communication module, a short-range wireless communication module, or a global navigation satellite system (GNSS) communication module) or a wired communication module 1794 (e.g., a local area network (LAN) communication module or a power line communication (PLC) module). A corresponding one of these communication modules may communicate with the external electronic device via the first network 1798 (e.g., a short-range communication network, such as Bluetooth™, wireless-fidelity (Wi-Fi) direct, or infrared data association (IrDA)) or the second network 1799 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 1792 may identify and authenticate the electronic device 1701 in a communication network, such as the first network 1798 or the second network 1799, using subscriber information (e.g., international mobile subscriber identity (IMSI)) stored in the subscriber identification module 1796.

The antenna module 1797 may transmit or receive a signal or power to or from the outside (e.g., the external electronic device) of the electronic device 1701. According to an embodiment, the antenna module 1797 may include an antenna including a radiating element composed of a conductive material or a conductive pattern formed in or on a substrate (e.g., PCB). According to an embodiment, the antenna module 1797 may include a plurality of antennas. In such a case, at least one antenna appropriate for a communication scheme used in the communication network, such as the first network 1798 or the second network 1799, may be selected, for example, by the communication module 1790 (e.g., the wireless communication module 1792) from the plurality of antennas. The signal or the power may then be transmitted or received between the communication module 1790 and the external electronic device via the selected at least one antenna. According to an embodiment, another component (e.g., a radio frequency integrated circuit (RFIC)) other than the radiating element may be additionally formed as part of the antenna module 1797.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 1701 and the external electronic device 1704 via the server 1708 coupled with the second network 1799. Each of the electronic devices 1702 and 1704 may be a device of a same type as, or a different type, from the electronic device 1701. According to an embodiment, all or some of operations to be executed at the electronic device 1701 may be executed at one or more of the external electronic devices 1702, 1704, or 1708. For example, if the electronic device 1701 should perform a function or a service automatically, or in response to a request from a user or another device, the electronic device 1701, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 1701. The electronic device 1701 may provide the outcome, with or without further processing of the outcome, as at least part of a reply to the request. To that end, a cloud computing, distributed computing, or client-server computing technology may be used, for example.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively," as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry." A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 1740) including one or more instructions that are stored in a storage medium (e.g., internal memory 1736 or external memory 1738) that is readable by a machine (e.g., the electronic device 1701). For example, a processor (e.g., the processor 1720) of the machine (e.g., the electronic device 1701) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a compiler or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

According to the embodiments disclosed herein, the electrode surface of the electronic device may have the specified hardness or more, thereby preventing the electrode surface from being damaged by external impact such as the friction and/or foreign matter.

Further, according to the embodiments disclosed herein, as the electrode of the electronic device has a resistance equal to or less than the specified resistance, the user's biometric information may be more accurately measured.

In addition, according to embodiments disclosed herein, it is possible to prevent the second conductive member connected to the PCB from being damaged during the process of forming the engraved identifier, which is formed in the high-hardness member constituting the electrode of the electronic device.

In addition, various effects that may be directly or indirectly identified through the specification may be provided.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:
1. An electronic device comprising:
   a housing comprising a first surface facing a first direction, a second surface facing a second direction opposite to the first direction, and a third surface connecting the first surface and the second surface to form a space in the housing;
   a display viewable in the first direction through the first surface of the housing;
   a printed circuit board (PCB) disposed in the space;
   a glass configured to cover at least a part of the second surface of the housing and including a fourth surface facing the first direction and a fifth surface facing the second direction;
   a high-hardness member disposed under the fifth surface;
   a first conductive member disposed between the high-hardness member and the glass; and
   a second conductive member disposed over the fourth surface and electrically connected to the PCB.

2. The electronic device of claim 1,
wherein the high-hardness member includes at least one of an oxide-based material, a nitride-based material, or a carbide-based material, and
wherein the first conductive member and the second conductive member each include at least one of chromium (Cr), titanium (Ti), gold (Au), silver (Ag), graphene, or carbon nano tube (CNT).

3. The electronic device of claim 1, wherein the first conductive member has a first thickness of between 1 micrometer (μm) and 100 μm.

4. The electronic device of claim 1, further comprising:
an adhesive member disposed between the glass and the first conductive member.

5. The electronic device of claim 4, wherein the adhesive member is formed by depositing or coating an adhesive material on the fifth surface.

6. The electronic device of claim 5, wherein the adhesive member is formed by depositing or coating silicon dioxide ($SiO_2$) on the fifth surface.

7. The electronic device of claim 4, wherein the adhesive member increases one or more of bonding energy of a surface of the first conductive member or the fifth surface or adhesion between the first conductive member and the glass.

8. The electronic device of claim 4, wherein the adhesive member is configured to prevent the first conductive member from being detached from the glass.

9. The electronic device of claim 1, further comprising:
a light blocking member disposed between the glass and the second conductive member.

10. The electronic device of claim 9, wherein the light blocking member comprises black carbon.

11. The electronic device of claim 9, wherein the light blocking member is formed on the fourth surface in a printing method.

12. The electronic device of claim 9, wherein the light blocking member is configured to prevent recognition of the PCB from outside when viewed in the first direction.

13. The electronic device of claim 1, further comprising:
an identifier engraved in the high-hardness member to allow at least a part of the first conductive member to be exposed in the high-hardness member,
wherein the second conductive member is configured to not overlap with the identifier in the first direction and in the second direction.

14. The electronic device of claim 13, wherein the second conductive member has a different area from an area of the first conductive member.

15. The electronic device of claim 13, further comprising:
a third conductive member configured to connect the second conductive member to the PCB.

16. The electronic device of claim 1, further comprising:
a connector formed in the first direction from the second conductive member and configured to connect the second conductive member to the PCB.

17. A wearable electronic device comprising:
a housing comprising a first surface facing a first direction, a second surface facing a second direction opposite to the first direction, and a third surface connecting the first surface and the second surface to form a space in the housing;
a display viewable in the first direction through the first surface of the housing;
a printed circuit board (PCB) disposed in the space;
a glass configured to cover at least a part of the second surface of the housing and including a fourth surface facing the first direction and a fifth surface facing the second direction;
a first electrode disposed on the glass and having a first voltage applied thereto;
a second electrode disposed on the glass to be adjacent to the first electrode and having a ground voltage applied thereto; and
a third electrode having a second voltage applied thereto having a polarity opposite to a polarity of the first voltage with regard to the ground voltage,
wherein the first electrode includes:
a high-hardness member disposed under the fifth surface,
a first conductive member disposed between the high-hardness member and the glass, and
a second conductive member disposed over the fourth surface and electrically connected to the PCB.

18. The wearable electronic device of claim 17,
wherein the first electrode and the second electrode each have a resistance of between 1 ohm (Ω) and 1 kiloohm (kΩ), and
wherein a resistance between the first electrode and the second electrode is between 1 gigaohm (GΩ) and 10 GΩ.

19. The wearable electronic device of claim 17,
wherein the first electrode is configured to measure an electrocardiogram (ECG) of a wearer wearing the wearable electronic device, and
wherein the high-hardness member is engraved with an identifier to expose at least a part of the first conductive member.

20. The wearable electronic device of claim 19,
further comprising a third conductive member configured to connect the second conductive member and the PCB,
wherein the second conductive member is configured to not overlap the identifier in the first direction and in the second direction.

21. The wearable electronic device of claim 17, further comprising:
a sensor configured to not overlap with the first and second electrodes and to measure a photo plethysmograph (PPG) of a wearer wearing the wearable electronic device.

22. The wearable electronic device of claim 21, wherein the sensor is disposed on the fifth surface.

23. The wearable electronic device of claim 22, wherein the sensor is disposed at a center of the fifth surface.

24. The wearable electronic device of claim 17, wherein the third electrode comprises a button formed on at least a part of the third surface of the housing or a ring formed using a conductive material constituting at least a part of the third surface.

25. The wearable electronic device of claim 17, wherein the third electrode comprises a transparent electrode constituting at least a part of the display.

* * * * *